United States Patent
Solomon et al.

(10) Patent No.: US 6,545,095 B1
(45) Date of Patent: Apr. 8, 2003

(54) PROCESS FOR MICROGEL PREPARATION

(75) Inventors: David Henry Solomon, Officer (AU); Greg Guanghua Qiao, Brunswick West (AU); Simmi Abrol, Wheelers Hill (AU)

(73) Assignee: University of Melbourne, Victoria (AU)

( * ) Notice: Subject to any disclaimer, the term of this patent is extended or adjusted under 35 U.S.C. 154(b) by 0 days.

(21) Appl. No.: 09/674,594

(22) PCT Filed: May 7, 1999

(86) PCT No.: PCT/AU99/00345

§ 371 (c)(1),
(2), (4) Date: Jan. 12, 2001

(87) PCT Pub. No.: WO99/58588

PCT Pub. Date: Nov. 18, 1999

(30) Foreign Application Priority Data

May 7, 1998 (AU) ................................................. PP3372

(51) Int. Cl.⁷ ...................... C08F 293/00; C08F 295/00; C08F 297/00; C08F 212/08; C08I 212/36
(52) U.S. Cl. ........................ 525/192; 525/193; 525/194; 525/195; 525/196
(58) Field of Search ................................. 525/192, 193, 525/194, 195, 196

(56) References Cited

U.S. PATENT DOCUMENTS 4,567,246 A * 1/1986 Gajria .................... 526/318.44
6,355,718 B1 * 3/2002 Berge et al. ................. 524/461

FOREIGN PATENT DOCUMENTS

| EP | 0 114 478 A1 | 8/1984 |
| WO | WO 96/30421 | 10/1996 |
| WO | WO 97/18247 | 5/1997 |
| WO | WO98/31739 | 7/1998 |

OTHER PUBLICATIONS

Derwent Abstract Accession No. 91–032005/05, and JP 2300203 A (Japan Synthetic Rubber), Dec. 12, 1990.
Copy of PCT International Search Report for PCT/AU99/00345 dated Jun. 21, 1999.

* cited by examiner

*Primary Examiner*—Nathan M. Nutter
(74) *Attorney, Agent, or Firm*—Andrew N. Parfomak; Norris, McLaughlin & Marcus, P.A.

(57) ABSTRACT

A process for producing a microgel composition particles having a core of cross-linked polymer at a multiplicity of polymeric arms appended to the core, the process comprising reacting a living prepolymer component with a monomer component wherein the monomer component includes a multi-olefininc monomer.

19 Claims, No Drawings

PROCESS FOR MICROGEL PREPARATION

The present invention relates to a process for the preparation of microgels and to a composition for use in such a process.

Microgels are macromolecules which possess a combination of very high molecular weight and a solubility and viscosity similar to linear or branched polymers of relatively low molecular weight. Microgels are an intermediate structure between conventional linear or branched polymers such as polyethylene or polycarbonate and networks such as vulcanised natural rubber. The dimensions of microgels are compatible with high molecular weight linear polymers but their structure resembles a network.

The properties of microgels make them particularly useful in a wide range of applications such as in additives, in advanced material formulations for foams or fibres, in coating compositions, binders and redispersible latexes. Microgels may also be used to improve the ease of processing and to improve the structural strength and dimensional stability of the final products. A further potential use for microgels is as additives for high impact polymers. Microgels embedded in a matrix of conventional linear polymer may act to stabilise the whole structure by distributing mechanical tension. Microgels are also useful in biological systems and as pharmaceutical carriers.

A number of methods have been used for the preparation of microgels, however these methods generally have a number of serious deficiencies. For example, extreme care is required in preparing microgels as the multiple double bonds present within these systems may readily undergo intermolecular reactions which can lead to intractable networks. Other procedures such as those described by OKay, O. and Funke, W. in *MACROMOLECULES*, 1990, 23 at 2623–2628 require high purity solvent and reagents as well as an inert atmosphere and are complicated by undesirable side reactions. Despite the unique properties of microgels the difficulties in preparing them have limited their potential and commercial use.

Our copending application PCT/AU98/00015 discloses a process for microgel preparation involving reacting an alkoxy amine with a cross-linking agent.

SUMMARY OF THE INVENTION

We have now found that Microgels may be prepared using a range of living radicals or macromonomers allowing the formation of microgels with a vast range of monomers and under a wide range of conditions.

Accordingly, we provide a process for producing a microgel composition comprising reacting a living prepolymer component with a monomer component including a multi-olefinic monomer. The microgel product typically comprises a cross-linked core and a multiplicity of polymeric chains appended to the cross-linked core. The polymeric chains appended to the core have free ends and may interact with solvent.

The term living prepolymer where used herein refers to a polymer having a radical-terminating group adapted to reversibly cleave from the polymer under activating conditions to provide a reactive prepolymer radical.

The reaction between the living prepolymer and monomer component may be conducted in the presence of an initiator and/or catalyst.

The proportion of cross-linked core in the microgel composition is determined by the ratio of living prepolymer to monomer component. Preferably, the molar ratio of living prepolymer to monomer component is in the range of from about 0.05/1 to about 5/1.

The monomer component used in the process of the invention comprises a multi-olefinic monomer. In the preferred embodiments of the invention the monomer component additionally includes a mono-olefinic monomer. The ratio of the number of moles of multi-olefinic monomer to the number of moles of mono-olefinic monomer will determine the density of the cross-linked core. The mono-olefinic monomer acts as a spacer and in high proportions reduces the density of the core.

A range of known techniques may be used to prepare the living propolymer component. Typically, the process includes reacting a mono-olefinic monomer and initiator optionally in the presence of a catalyst. The mono-olefinic monomer used in preparation of the living prepolymer component may include monomer containing more than one double bond and which reacts to provide chain extension rather than cross-linking. Examples of such monomers include conjugated dienes and 1,5-dienes.

Throughout the description and claims of this specification, the word "comprise" and variations of the word, such as "comprising" and "comprises", is not intended to exclude other additives or components or integers.

Methods for Preperation of Living Prepolymer

The living prepolymer may have a radical terminating group adapted to reversibly cleave from the prepolymer under activating conditions to provide a reactive prepolymer radical.

Examples of radical terminating group precursors include Lewis acids, mercaptans, disulfides, thiocarbamates and dithiocarbamates, dithioesters, transition metal carbonyls, stabilized carbon radicals, peroxides and azo initiators.

Typical examples of Lewis acid radical terminating group precursors include metal complexes such as $CuX/2,2'$-bipyridines, $Mn(CO)_6RuX_x/PPh_3$, $AR(OR)_3$, $NiX/O,O'$—$(CH_2Nme_2)C_6H_3$, $NiX_2/PPh_3$ and $FeX_2/N(n\text{-}Bu)_3$ wherein X is halogen and preferably chlorine or bromine. Lewis acid terminated prepolymer radicals may be prepared by a method of atom transfer radical polymerization which is hereinafter described.

The method of atom transfer radical polymerization (ATRP) may be represented as shown in the following scheme:
Initiation:

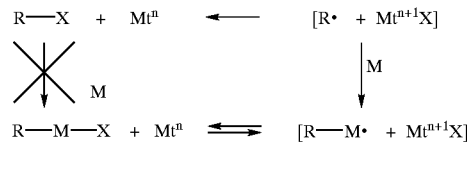

Propagation:

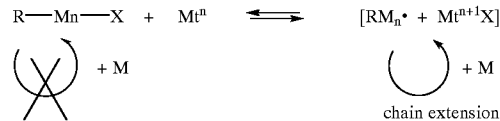

Initially, the transition metal species, $M_t^n$, abstracts the halogen atom X from the organic halide, R—X, to form the oxidized species, $M_t^{n+1}X$, and the carbon-centered radical R. In the subsequent step, the radical R., reacts with unsaturated monomer, M, with the formation of the intermediate radical species, R—M. The reaction between $M_t^{n+1}X$ and R—M results in the target product, R—M—X, and regenerates the reduced transition metal species, $M_t^n$, which further reacts with R—X and promotes a new redox cycle. When polymeric halides, R—M—X, are reactive enough toward $M_t^n$ and monomer is in excess, a number of atom transfer radical additions, i.e., a "living"/controlled radical polymerization occurs. Further, details of this mechanism are described in the reference: Macromolecules, 1995, 28, 7901.

Another embodiment of ATRP is described in Macromolecules, 1995,28,7970 and Macromolecules, 1996, 29,3665. These references report on the formation of "living" polymers using a combination of an arylsulfonyl chloride and a transition metal compound.

One part of the polymerization system in the process is an arylsulfonyl halide or an alkyl sulfonyl halide of the formula $A^1SO_2X$ wherein $A^1$ is an aryl, substituted aryl group, an alkyl group or a substituted alkyl group, and X is chlorine, bromine or iodine. Included within the meaning of arylsulfonyl halide and alkylsulfonyl halide is any adduct, such as a 1:1 adduct, which is a reaction product of an aryl or alkyl sulfonyl halide and any polymerize vinyl monomer. In effect, such an adduct is one of the initial products in the polymerization process itself.

Another component of the ATRP system is a compound containing a lower valent transition metal atom. By this is meant a compound containing at least one transition metal atom that is capable of existing in a higher valent state. Included within the definition of a compound containing a transition metal atom in a lower valent state is a compound or combination of compounds that under the polymerization process conditions can form in situ the desired compound containing a transition metal atom in a lower valent state. In some cases this can include metal itself (or an alloy or a metal oxide thereof) which can either be dissolved or slightly dissolve in the process medium.

Suitable lower valent metals include Cu[I], Ru[I], Ni[II], Re[II], Pd[II], Cu[0], Ni[0], Fe[0], Pd[0], and Rh[II]. The transition metal compound should preferably be at least slightly sole in the polymerization medium. Optionally the transition metal compound which is added may be solublized by the addition of certain complexing agents.

The molar ratio of lower valent transition metal compound:arylsulfonyl halide or alkyl sulfonyl halide is not critical, but it be preferred that it be greater than 0.2, more preferably greater than 0.5, especially if a living polymerization is desired. It is also preferred that this ratio not be over 5 and more preferably be less than 2.

Many living polymers which are useful in the process of the invention may be formed from iniferters, that is initiators which form two radicals one of high activity which reacts with monomer and another of relatively low activity capable of reversibly terminating the growing radical. The preferred iniferters also provide chain transfer with a propagating carbon radical. The preparation of trapped radical adducts from iniferters may be represented as shown below:

Initiation: I–I'→I.+I'.
Propagation: I.+M→I M.→I(M)$_n$M.
Termination:
 I(M)$_n$M.+I'.⇌I(M)$_n$M I'
 I(M)$_n$M.+I–I'→I(M)$_n$M–I'+I.

Living polymers comprising thiocarbamate, dithiocarbamate, dithioester and stabilized carbon radicals may be prepared by this method.

Living polymers containing thiocarbamates or dithiocarbamates are preferably of formula I or II;

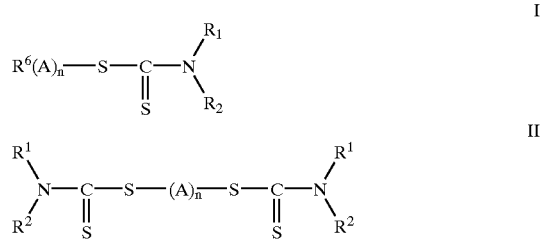

wherein $R^6$ is hydrogen or an initiator fragment residue, $R^1$ and $R^2$ are independently selected from hydrocarbyl, particularly $C_1$ to $C_6$ alkyl and A is a monomer unit.

Examples of iniferters which may be used in preparation of living polymers containing thiocarbamates or dithiocarbamates include compounds of formulation Ia and IIa

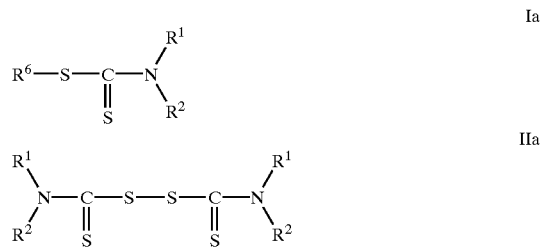

The living prepolymer may comprise a thiocarbonylthio radical terminating group. Examples of such compounds are of formula:

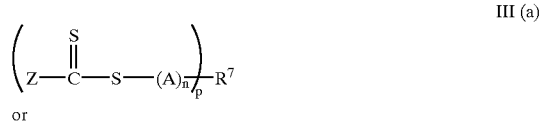

or

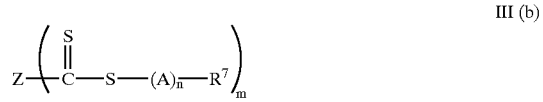

X wherein Z is a group chosen such that the chain transfer constant is in the desired range. Suitable Z groups are hydrogen, optionally substituted alkyl, optionally substituted aryl, optionally substituted alkoxy, optionally substituted alkylthio, chlorine, optionally substituted alkoxycarbonyl, optionally substituted aryloxycarbonyl, carboxy, optionally substituted acyloxy, optionally substituted carbamoyl, cyano, dialkyl- or diarylphosphinato-, dialkyl or diarylphosphenato and polymer chain;

$R^7$ is an optionally substituted alkyl, optionally substituted alkenyl, optionally substituted alkynyl, optionally substituted (saturated, unsaturated or aromatic) carbocyclic/heterocyclic ring, optionally substituted alkylthio or other group such that $R^7$ is a free radical leaving group under the polymerization conditions and is capable of initiating free radical polymerization; $R^7$ may also be a polymer chain prepared by any polymerization mechanism or an organometallic species; and m and p are integers and preferably are at least 2.

The living prepolymers of formula IIIa and IIIb may be prepared by reaction of a vinyl monomer with a thiocarboxylthio chain transfer compound of any of formulas IV(a), IV(b) or IV(c). The reaction will usually be initiated by free radicals produced from a free radical source.

The monomer used in preparing the living polymer may have the formula $CH_2=CUV$ in which case the resulting monomer unit "A" in the compound of formula III(a) or III(b) will have the formula:

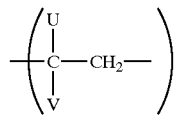

wherein U is selected from the group consisting of hydrogen, halogen, optionally substituted $C_1$–$C_4$ alkyl wherein the substituents are independently selected from the group that consists of hydroxy, alkoxy, aryloxy (OR"), carboxy, acyloxy, aroyloxy ($O_2CR$"), alkoxy-carbonyl and aryloxy-carbonyl ($CO_2R$");

V is selected from the group consisting of hydrogen, R", $CO_2H$, $CO_2R$", COR", CN, $CONH_2$, CONHR", CONR"$_2$, $O_2CR$", OR" and halogen;

R" is selected from group consisting of optionally substituted alkyl, an optionally substituted saturated, unsaturated or aromatic carbocyclic or heterocyclic ring; optionally substituted alkylthio; optionally substituted alkoxy, optionally substituted dialkylamino; an organometallic species, and a polymer chain prepared by any polymerixation mechanism;

The monomer may also be selected from the group consisting of maleic anhydride, N-alkylmaleimide, N-arylmaleimide, dialkyl fumarate and cyclopolymerizable monomers.

Preferred dithioester chain transfer agents for use in preparing prepolymers of formula IIIa and IIIb are represented by formulas IV a–c.

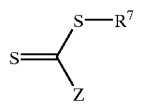

IVa

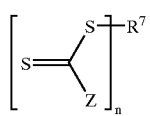

IVb

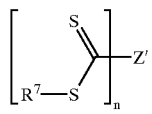

IVc

In formula IVa:

R$^7$ is an optionally substituted alkyl, optionally substituted alkenyl, optionally substituted alkynyl, optionally substituted (saturated, unsaturated or aromatic) carbocyclic/ heterocyclic ring, optionally substituted alkylthio or other group such that R$^7$. is a free radical leaving group under the polymerization conditions and is capable of initiating free radical polymerization. R$^7$ may also be a polymer chain prepared by any polymerization mechanism or an organometallic species.

In formula IVb:

n is an integer greater than 1.

R$^7$ is a group derived from substituted alkyl, substituted aryl or a polymer chain, or other group such that R$^7$. is a free radical leaving group under the polymerization conditions and is capable of initiating free radical polymerization; and Z is as defined for Formula III.

In Formula IVc:.

n is an integer greater than 1.

Z' is a group derived from optionally substituted alkyl, optionally substituted or a polymer chain where the connecting moieties are selected from aliphatic carbon, aromatic carbon, oxygen or sulfur; and R$^7$ is as defined in Formula IVa.

Other multifunctional thioesters and dithioesters as follows:

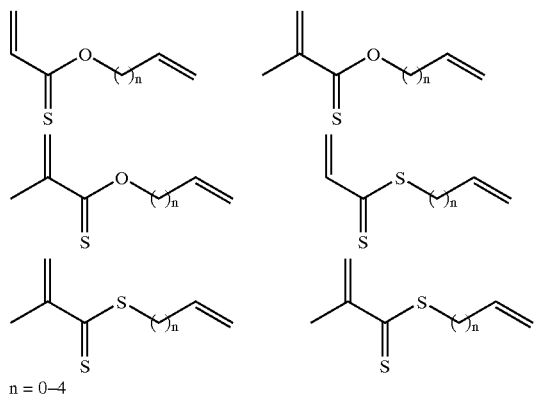

n = 0–4

A more complete description of the dithioester chemistry is contained in International Patent Application PCT/US97/12540 (WO 98/01478) in the name of E.I. Du Pont De Nemours and Company the contents of which are herein incorporated by reference.

Living prepolymers containing stabilized carbon-radical terminating groups are preferably of formula V.

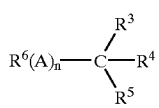

V wherein R$^2$ and R$^4$ are independently selected from tertiary alkyl and aryl and most preferably aryl such as phenyl; R$^6$ is an initiator fragment residue preferably selected from tertiary alkyl, aryl and the group —C(R$^8$R$^9$R$^{10}$); and R$^5$, R$^8$, R$^9$ and R$^{10}$ are independently selected from tertiary alkyl, aryl, nitrile, alkoxy, aryloxy and trimethylsiloxy.

Adducts containing stabilized carbon-radical terminating groups may be prepared from compounds of formula VI or VII.

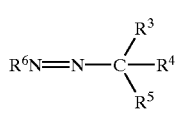

VI

-continued

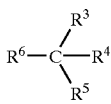

VII wherein $R^3$, $R^4$, $R^5$ and $R^6$ are as hereinbefore defined.

The compound of formula V may be prepared by decomposing the compound of formula VI in the presence of monomer A.

The most preferred compound of formula VI is phenylazotriphenyl-methane (PAT).

Examples of the use of iniferters are described by Otsu and Yoshisha Makromol Chem; Rapid Commun. 3:127 (1982) and 3:113 (1982).

Examples of azo and peroxide adducts include compounds of formula VIII and IX

VIII

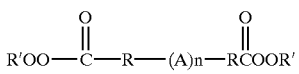

IX wherein R and $R^1$ are hydrocarbyl and preferably alkyl.

Examples of the radical adducts of formulas VIII and IX may be prepared from the multifunctional compound of formula X.

X by activating the perester group in the case of compounds of formula X or the azo group in the case of compounds of formula VIII. Examples of multifunctional initiators such as di-t-butyl-4,4'-azobis(4-cyanoperoxy valerate) are disclosed by Piirma et al., J. Appl. Poly. Sci. 24:2051 (1979), J. Appl. Polym. Sci 26:3013 (1981) and J. Appl. Polym. Sci 33:717 (1987).

Living prepolymers containing an azo group as a link between oligomer chains may be prepared by reacting and anionic oligomer with an azobis(isobutylronitrile) (AIBN) according to the scheme.

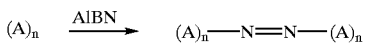

Such a procedure is disclosed by Reeb et al., Eur. Polym. J. 12:317 (1976) and Poym. Prepr., Am. Chem. Soc., Div. Polym., Chem., 21:55 (1980).

An analogous procedure may be used to prepare peroxy containing living prepolymer by reacting an anionic oligomer with p,p'-bis(bromomethyl)benzoyl peroxide in the presence of a promoter such as butyl lithium. Examples of such a process are disclosed by Riess et al., Eur. Polym. J. 11:301 (1975) and lnf. Chim. 116:117 (1973).

Living prepolymers having sulfur containing trapping groups may be derived from mercaptans of formula XI or XII

XI

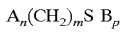

XII wherein A and B are monomers which may be the same or different.

Such mercaptans may in turn be prepared by a range of methods known in the art. In a preferred example, adducts of formula XI or XII wherein m is 2 are prepared by reaction of an anionic prepolymer (A)⁻ with a thiirane to cause ring opening and provide a 2-thiolethyl substituted prepolymer of formula XI and optionally reacting the 2-thiolethyl substituted polymer with a monomer (B), which may be the same as A or different from A, to provide a prepolymer of formula XII.

In the compounds of formula I to XII the monomer A or B and monomer units —(A)— may have the formula defined for monomer A and monomeric unit (A) in thioesters IIIa and IIIb.

Another class of living prepolymer useful in the process of the invention are macromonomers depicted by formula XIII. In particular, macromonomers containing a maximum of 2 double bonds more preferably 1 double bond, per polymer chain.

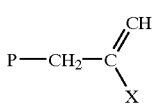

XIII

Where X is —$CONR_2$, —COOR, $OR^1$, —OCOR, —$OCOOR^1$, —$NRCOOR^1$, halo, cyano, or a substituted or unsubstituted phenyl or aryl, wherein R is independently selected from the group of hydrogen, silyl, or a substituted or unsubstituted alkyl, alkyl ether, phenyl, benzyl, or aryl, wherein said groups may be substituted with epoxy, hydroxy, isocyanato, cyano, amino, silyl, acid (—COOH), halo, or acyl; and wherein $R^1$ is the same as R except not H.

Macromonomers of this type can be prepared by a number of different methods. Two methods of preparation, included for illustration purposes but not meant to be limiting, are:

1) catalytic chain transfer agents containing Co2+ Co3+ as described in U.S. Pat. Nos. 5,362,826, 5,324,879 and WO 9731030 which is equivalent to U.S. Pat. No. 6,100,350, the contents of which are incorporated by reference.

2) Addition-fragmentation polymerization as described in PCT/US95/14428 (WO 960704) which is equivalent to U.S. Pat. No. 5,756,605 and to U.S. Pat. No. 6,291,620 the contents of which are incorporated by reference.

The macromonomer may be used as a living prepolymer in the process of the invention or may be modified to provide a radical terminating group adpated to reversibly cleave from the prepolymer under activating conditions. In one embodiment a double bond of the macromonomer is converted and provide a capped radical by any of a range of methods depending on the type of radical terminating group to be used. For example, an alkoxy amine terminating group may be provided by reaction with an oxygen activating group such as a butoxide followed by reaction with a hindered nitroxide. Alternatively a group suitable for ATRP may be incorporated by reaction with an appropriate brominating agent, such as hexadecyltrimethylphosphoniumbromide, to form a bromide. Other examples of modified macromers will be readily apparent from the above described prepolyers of formulae I to XIII.

The oligomer $(A)_n$ component of the trapped radical adduct will comprise one or more monomers however, it is particularly preferred that the living prepolymer is an oligomer comprising at least 3 monomer units and more preferably at least 5 monomer units. The molecular weight of the living prepolymer radical is preferably from 500 to 100,000, more preferably 1000 to 25,000, and most preferably from 3000 to 15,000.

The above described prepolymer may also be used to produce the functionalized polymer, such as hydroxy substituted polymer and converted into a radical terminating group adapted to reversibly cleave from the prepolymer under activating conditions. This modified prepolymer can then be chain expended by another monomer to form copolymerized arms. The ratio of the two types of the monomer units can be used to control the hydrophilic properties of the arm. By increasing the proportion of functional groups such as hydroxy groups the resulting arms become more hydrophilic.

The monomers with functional groups, such as hydroxy group, may be used alone or mixed with other monomers in the arm using one of the above described controlled polymerization methods. The ratio of the functionalized monomer to the un-functionalized monomers controls the hydrophilic and hydrophobic balance of the arms and hence the final microgels.

Preparation of Microgel

When the living prepolymer includes at least three monomer units (preferably at least 5), the resulting microgel takes the form of linear arms of prepolymer linked to a crosslinked network forming a core. This type of microgel may conveniently be referred to as a star microgel.

The proportion of components used in the process of the invention will generally depend on the desired properties of the microgel and the intended application. Generally, the microgel is prepared using up to 60 mole percent of crosslinking agent based on moles of polymerizable components. More preferably the crosslinking agent will comprise up to 50 mole percent of the total of the polymerizable components. Typically the trapped radical adduct will comprise from about 5 to about 95 mole percent of the polymerizable components.

The present invention allows a higher proportion of crosslinking agent than has previously been possible for microgel compositions. Prior art microgels have generally been restricted to using no more than several mole percent of crosslinking agent. The ability to use high concentrations of crosslinking agent enables microgels to be prepared with a high density conferring significant advantages in rheology control. Accordingly, it is preferred that the process of the invention use at least 5 mole percent of crosslinking agent based on total of the polymerizable components and most preferably from 10 to 50%.

In the process of the present invention when the average number of monomeric units in the oligomer portion of the living prepolymer is less than 5 monomeric units it is particularly preferred that the monomer composition include a further monomer selected from monounsaturated monomers and conjugated diene monomers. As the average number of monomer units in the oligomer portion of the adduct decreases, the improvement provided by using monomer becomes more significant. When the number of monomeric units in the oligomer is from 1 to 3 a monounsaturated monomer is typically used.

Typically the unsaturated monomer is present in up to 80 mole percent based on the total number of moles of the polymerizable components and more preferably from 10 to 80%.

When the number of monomer units present in the prepolymer is less than 5, the adduct is preferably present in an amount of from 5 to 60 mole percent.

Star microgels are preferably prepared using from 50 to 95 mole percent of adduct and up to 45 mole percent of monounsaturated monomer.

The one or more further monomers when used in the process of the invention may be any well known monounsaturated monomer such as an alkene, acrylate, methacrylate, styrene or styrenic monomer, acrylonitrile or substituted acrylonitrile, or a conjugated diene monomer such as butadiene, isoprene, chloroprene, cyclopentadiene vinyl acetate, vinylidene chloride and polyvinylidene dichloride.

The properties of the microgel and its reactivity in subsequent applications may be controlled by the choice of monomers and their functional groups. Examples of monomers include $C_1$ to $C_{10}$ alkenes, alkylacrylates, alkylmethacrylates, hydroxyalkylacrylates, hydroxyalkylmethacrylates, haloalkylacrylates, haloalkylmethacrylates, alkoxyalkylacrylates, alkoxyalkylmethacrylates, optionally mono- N-substituted or di-N-substituted aminoalkylmethacrylates, cycloalkylaerylates, cycloalkylmethacrylates, phenoxyacrylate, phenoxymethacrylate, alkylene glycolacrylate, alkylene glycol methacrylate, polyalkyleneglycolacrylate, polyalkyleneglycolmethacrylate, acrylamides, methacrylamides, derivates of acrylamindes and methacylamides, esters of fumaric acid, maleic acid and maleic acid anhydride and esters of maleic acid, N-vinyl cae, N-vinylpyrrolidone, vinyl pyridine, acrylate and benzyl methacrylate.

The oligomer, $(A)_n$ portion of the prepolymer may be a homopolymer or a copolymer.

When the oligomer is a copolymer, it may be a statistical or a block copolymer. The monomers used in preparing the oligomer may include one or more functional groups in addition to the double bond. These additional functional groups may be selected to confer the desired polarity or reactivity on the arms of the star type microgel. Examples of additional functional groups include halo, amino, hydroxy, carboxyl, mercapto, substituted amino, silane groups and epoxy. Hydroxy functional groups such as in the monomer hydroxyethyl methacrylate are particularly preferred. A monomer which includes the additional functional group or groups may form a homopolymer or a comonomer of a statistical or block copolymer.

The monomer units present in the prepolymer may be the same or different. Statistical copolymers may be prepared by using a mixture of monomers and block copolymers may be prepared by introducing monomers in sequence to provide a block of the first monomer before the second is introduced.

The multiolefinic compound used in the process of the invention preferably contains two or more double carbon-carbon bonds. Other functional groups such as hydroxyl, carboxyl, ester, amide amino, substituted amino, mercapto, silane and epoxy or the like may be present if desired. Examples of suitable multi-olefinic compounds include divinyl benzene and derivatives of divinyl benzene and monomers containing two or more acrylate or methacrylate functional groups. Examples of such polyacrylate compounds include polyols substituted with two or more double bonds derived from acrylic or methacrylic acids. Examples of di- and tri-acrylate compounds include compounds of formula XIV;

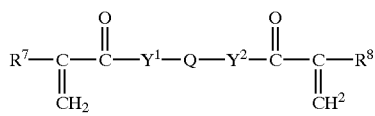

XIV wherein $R^7$ and $R^8$ are independently selected from hydrogen, halogen $C_1$ to $C_6$ alkyl preferably methyl and substituted $C_1$ to $C_6$ alkyl such as $C_1$ to $C_6$ hydroxyalkyl;

- $Y^1$ and $Y^2$ are independently selected from $NR^9$ and O where $R^9$ is independently selected from hydrogen and alkyl; and
- Q is a linking group which may be any linking group known in the art. Preferred linking groups include alkylene (preferably of 1 to 12 carbon atoms), a carbocyclic or heterocyclic group or polyalkylene oxide and wherein the groups may optionally be substituted with one or more substituents selected from halo, hydroxy, amino, substituted amino, silane, epoxy, acrylate or methacrylate.

Preferably Q is alkylene of 1 to 10 carbon atoms or a polyalkylene oxide and optionally include a substiuent selected from hydroxy, amino silane, epoxy and acrylate or methacrylate. When one or both of $R^7$ and $R^8$ are substituted alkyl, suitable substituents include hydroxy, halo, amino, substituted amino, thiol, silane and epoxy.

Preferred polyacrylate compounds include trimethylol propane triacrylate, trimethylol propane trimethacrylate, pentaerythritol tetraacrylate, pentaaerythritol tetramethacrylate, alkylene glycol diacrylates, alkylene glycol dimethacrylates, diacrylates of polyalkylene glycols, dimethacrylates of polyalkylene glycols diacrylates of polyoxyalkyleneglycol, dimethacrylates of polyoxyalkyleneglycol, 2-cyanoethylacrylate, alkylene glycol acrylate methacrylate, polyalkyleneglycol acrylate methacrylate, polyoxyalkkylene glycol acrylate methacrylate. Specific example of multi-olefinic compounds include divinyl benzene, ethylene glycol dimethacrylate, butanediol dimethacrylate, triethylene glycol diacrylate, 1,6-hexanediol diacrylate, trimethylolpropane triacrylate, triethylene glycol diacrylate, pentaerythritol triacrylate, 1,3-butylene glycol diacrylate and ethylene glycol acrylate methacrylate or other polyol acrylate methacrylates.

Allyl and substituted allyl derivatives, such as esters of acrylic and methacrylic acid, ethers and amines may also be used as multi-olefinic compounds. Some examples are listed below:

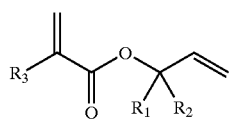

Where $R_1$ = H or alkyl
$R_2$ = H or alkyl
$R_1$ and $R_2$ may contain functional groups, ie. hydroxy.
where $R_3$ = H or methyl Allyl Acrylates:

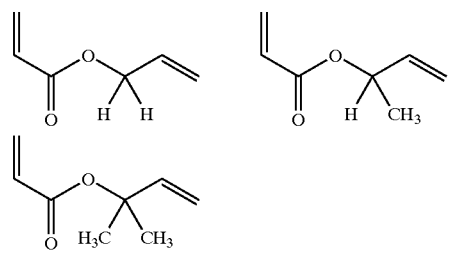

where $R_1=R_2=H$
$R_1=H, R_2=CH_3$
$R_1=R_2=CH_3$

Allyl Methacrylates:

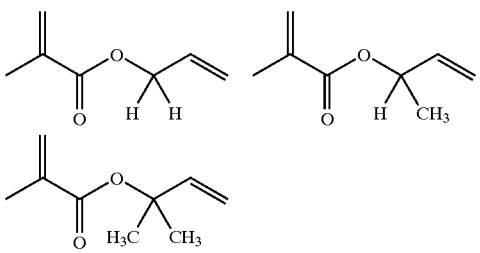

where $R_1=R_2=H$
$R_1=H, R_2=CH_3$
$R_1=R_2=CH_3$

Diallyl Ethers:

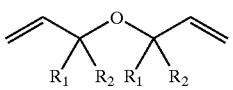

Where $R_1$ = H or alkyl
$R_2$ = H or alkyl
$R_1$ and $R_2$ may contain functional groups, ie. hydroxy.
$R_1$ and $R_2$ can also form unsymmetrical structures Examples:

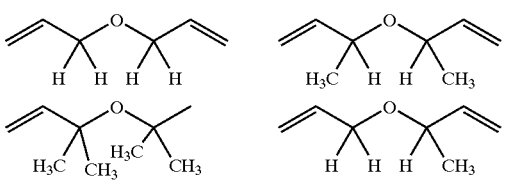

Diallyl Amines:

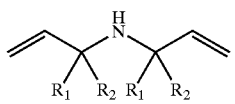

Where $R_1$ = H or alkyl
$R_2$ = H or alkyl
$R_1$ and $R_2$ may contain functional groups, ie. hydroxy.
$R_1$ and $R_2$ can also form unsymmetrical structures Examples:

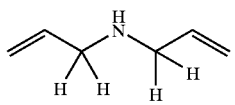 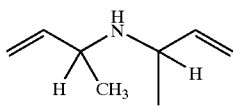

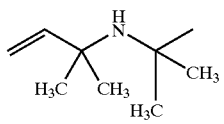 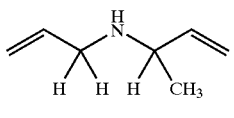

Triallyl Amines:

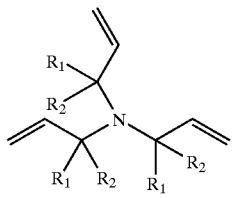

Where $R_1$ = H or alkyl
$R_2$ = H or alkyl
$R_1$ and $R_2$ may contain functional groups, ie. hydroxy.
$R_1$ and $R_2$ can also form unsymmetrical structures Examples

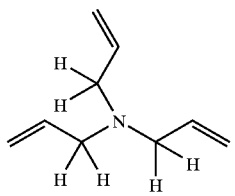 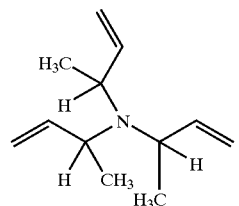

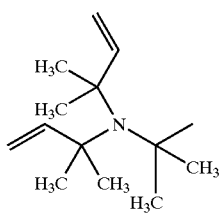

Other unsubstituted compounds:

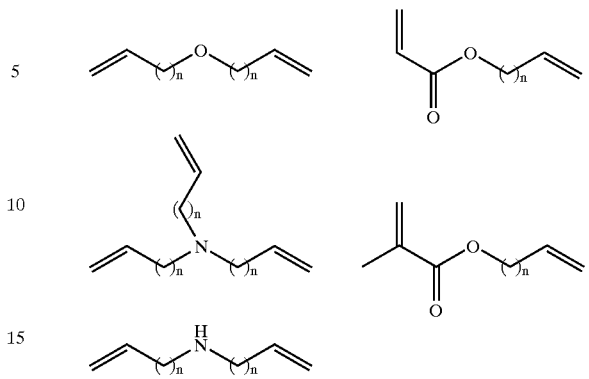

where n=0–4

The choice of crosslinking agent may be used to control the architecture and chemical properties of the crosslinked network which constitutes the core of the star type microgel. Three general types of multi-olefinic compounds may be used depending on the properties required.

When the unsaturated groups in the crosslinking monomer are equivalent, their relative reactivity is determined by statistical considerations. A greater degree of control is provided when the unsaturated groups have different reactivities. Without wishing to be bound by theory, we believe the greater control provided by using unsaturated group of different reactivities occurs due to the occurrence of chain growth at one of the double bonds prior to completion of crosslinking. The other type of crosslinking agent which may be used includes additional functional groups which may be selected to provide the desired interaction with solvents or other species or the reactivity of the microgel. These three groups of crosslinkers will be discussed in more detail.

Examples of multi-olefinic compounds in which the vinyl groups are of equivalent reactivity include divinyl benzene and compounds of formula XIV wherein $R^7$ and $R^8$ are the same and Q is unsubstituted or has symmetrical substitution. Other commercially available monomers of this type include alkylene glycol diacrylates and dimethacrylates such as diacrylate or butanediol dimethacrylate.

Examples of multi-olefinic compounds in which the vinyl groups have different reactivities include compounds of formula XIV wherein $R^7$ and $R^8$ are different and/or $Y^1$ and $Y^2$ are different. Such multi-olefinic compounds contain two different unsaturated groups selected from acrylate, methacrylate, acrylamide and methacrylamide. The two different saturated groups may be linked for example by alkylene glycol or polyalkylene glycol linking groups. Particularly preferred multi-olefinic compounds with distinct vinyl groups include the following:

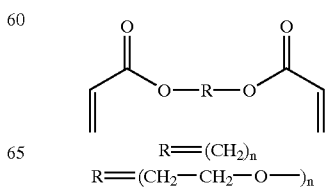

$R = (CH_2)_n$
$R = (CH_2 - CH_2 - O -)_n$

-continued

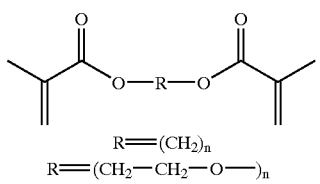
R=(CH₂)ₙ
R=(CH₂—CH₂—O—)ₙ

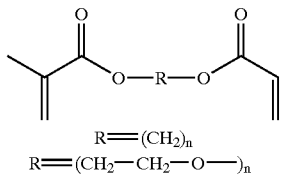
R=(CH₂)ₙ
R=(CH₂—CH₂—O—)ₙ

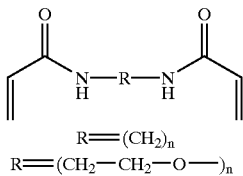
R=(CH₂)ₙ
R=(CH₂—CH₂—O—)ₙ

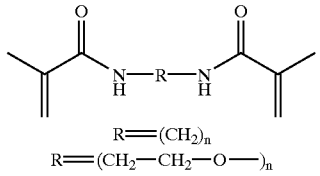
R=(CH₂)ₙ
R=(CH₂—CH₂—O—)ₙ

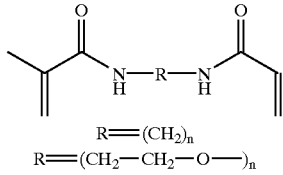
R=(CH₂)ₙ
R=(CH₂—CH₂—O—)ₙ

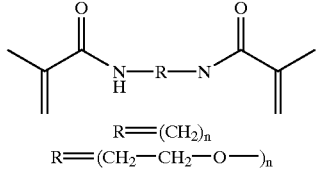
R=(CH₂)ₙ
R=(CH₂—CH₂—O—)ₙ

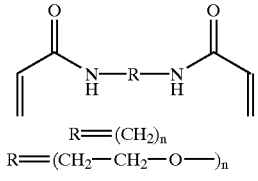
R=(CH₂)ₙ
R=(CH₂—CH₂—O—)ₙ

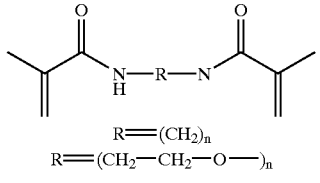
R=(CH₂)ₙ
R=(CH₂—CH₂—O—)ₙ

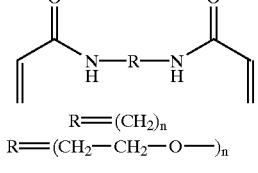
R=(CH₂)ₙ
R=(CH₂—CH₂—O—)ₙ

-continued

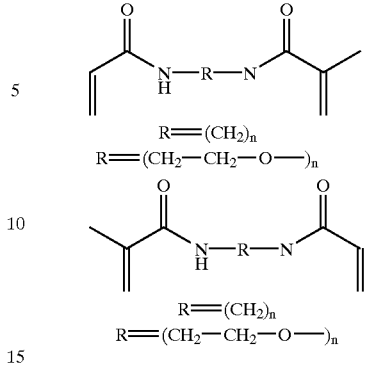
R=(CH₂)ₙ
R=(CH₂—CH₂—O—)ₙ

R=(CH₂)ₙ
R=(CH₂—CH₂—O—)ₙ

Another group of multi-olefinic compounds which are useful in the invention are compounds which in addition to at least two unsaturated groups further include one or more other functional groups such as hydroxyl, mercapto, amine, halo amido and alkoxy carbonyl. Substituted compounds of this general type are particularly useful in producing star type microgels having a hydrophilic core or a core including reactive groups. Specific examples of such multi-olefinic compounds include hydroxy substituted compounds such as pentaerythritol triacrylate and compounds of formula XIV wherein Q includes one or more substituents selected from hydroxyl, amino, substituted amino, silane, epoxy acrylate, alkylene acrylate, methacrylate and alkylene methacrylate.

The invention may use a mixture of multi-olefinic compounds. For example, the use of multi-olefinic compounds from different classes such as divinyl benzene and diacrylates or dimethacrylates may provide advantages. Further, combinations of symmetrical multi-olefinic compounds and multi-olefinic compounds having double bonds of different reactivities can be used to control crosslinking density.

Allyl and substituted allyl derivatives may be used alone as crosslinker or used in combination with other crosslinkers to control the density of the core of the formed star polymers.

The process of the invention may be conducted in the presence of a solvent, if desired. The process may, for example, be conducted in solution, in bulk or in suspension.

In preparation of star microgels the reaction is preferably conducted in a suitable solvent for the oligomer and theta-solvents are particularly preferred. We have found that in some cases the crosslinking reaction is highly efficient when a mixture of crosslinking agent and a monomer containing one unsaturated group is employed and believe the role of the monomer is to act as a spacing unit. It is also preferred that the spacing monomer solvate the arms of the star-type microgel which are derived form the oligomer.

Without wishing to be bound by theory we believe that the monomer diluent acts as a spacer monomer to control crosslinking density and to improve the efficiency of crosslinking. In some systems it may be difficult to obtain efficient crosslinking and microgel formation in the absence of a suitable monomer such as monounsaturated monomer.

The spacer monomer may comprise a monomer having one or more additional functional groups to provide a means for controlling the reactivity or chemical properties of the microgel. For example, in one embodiment the spacer monomer comprises at least two types of monomers including a monomer which provides a relatively inert monomer unit and a functionalized monomer incorporating one or more additional functional groups such as hydroxyl, carboxyl, amides, amino substituted amino, thiol, silane, epoxy or the like.

The spacing monomer may be the same or different from the monomer used in preparing the oligomer. However, in many cases it is convenient to use the same monomer. The spacer monomer is typically in the range of from 0 to 70 mole percent of the polymerizable components and preferably from 5 to 70 mole percent.

The process of the present invention generally has the significant advantage over prior art processes for forming microgels that it allows oligomer arms to be incorporated much more efficiently so that the proportion of unreacted residual monomer in the resulting microgel is reduced.

The microgel prepared in accordance with the process of the invention generally has a number average molecular weight of at least about $10^4$. Preferably, the molecular weight is in the range of from about $10^4$ to $10^7$ and most preferably from about $10^5$ to about $10^7$.

The microgels prepared according to the process of the invention have a range of applications.

The microgels are particularly useful as rheology control agents in solvent-borne and waterborne coatings.

In formulating coating composition it has been necessary to compromise between providing maximum solids content and providing good durability. Whereas high solids content is best satisfied by using a low molecular weight polymer durability is best satisfied by high molecular weight. The microgels of the present invention allow the compromise to be more effectively met by providing a polymer of high molecular weight, and hence providing good durability while at the same time providing the solubility to enable a high solids content to be achieved. The microgels also allow a reduction in solvent content to be achieved without the problems of sagging which occur with lower molecular weight resins.

The microgels of the invention may be used in thermosetting or radiation curable compositions. Such compositions will generally comprise a microgel which comprises pendant functional groups which may be provided by using a monomer, alkoxyamine or crosslinking agent which has the appropriate functional group such as a hydroxy, amino, carboxyl mercapto, substituted amino, silane, carbamate or epoxy group. The crosslinking agent will contain functional groups which are reactive with the pendant functional group of the microgen under the curing conditions.

The microgels of the invention may also be used in adhesives and cosmetics.

The microgels prepared according to the invention are also useful as plastic additives to improve impact resistance and to provide internal lubrication. The microgel prepared according to the invention is also useful as a pharmaceutical carrier particularly when prepared using polar functional groups which may facilitate association of the microgel with the pharmaceutical.

The following examples are provided for the purpose of further illustration of the present invention but are in no way to be taken as limiting.

EXAMPLE 1 a) Preparation of PS Arms End-capped with Cl Atom by ATRP Method

Initiation

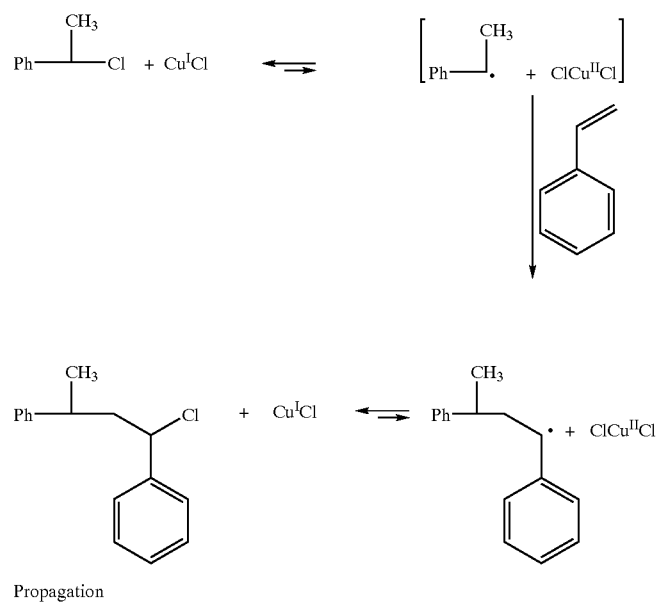

Propagation

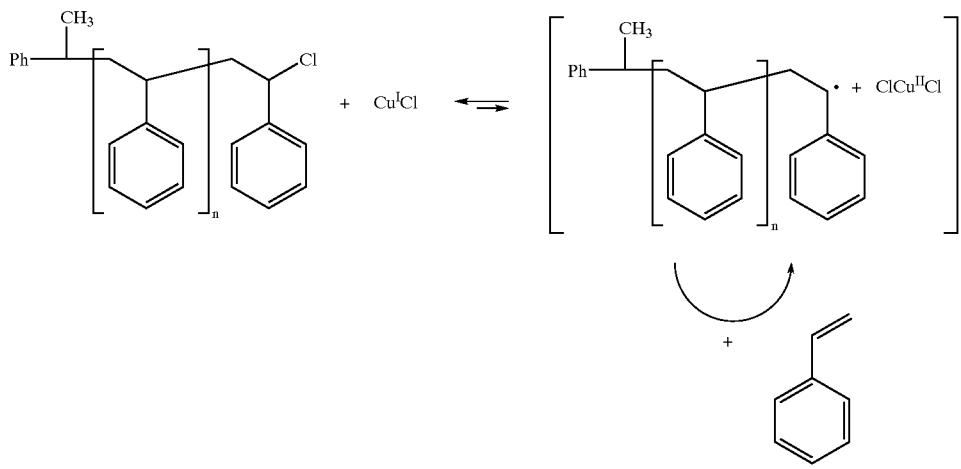

Styrene (23.5 mmol, 2.7 ml), CuCl (0.553 mmol, 0.055 g), 2,2'-bipyridine (bpy, 1.66 mmol, 0.259 g) and 1-phenylethyl chloride (1-PECl, 0.553 mmol, 73 μl) were added to a dry Schlenk flask. The mixture was degassed via 3 freeze-pump-thaw cycles before it was immersed in an oil bath at 130° C. with stirring. After 5 h of polymerization, the solution was diluted with THF. It was then filtered and passed through alumina (Brockmann I, neutral) in a column to remove the copper complex. The polystyrene (PS) formed was precipitated from MeOH (3 times) and dried at 60° C. under vacuum for 48 h. The MW of the polymer obtained as measured by GPC was Mn=4696 (PD=1.33) and with 23.61% conversion b) Microgel Formation with DVB by ATRP Method

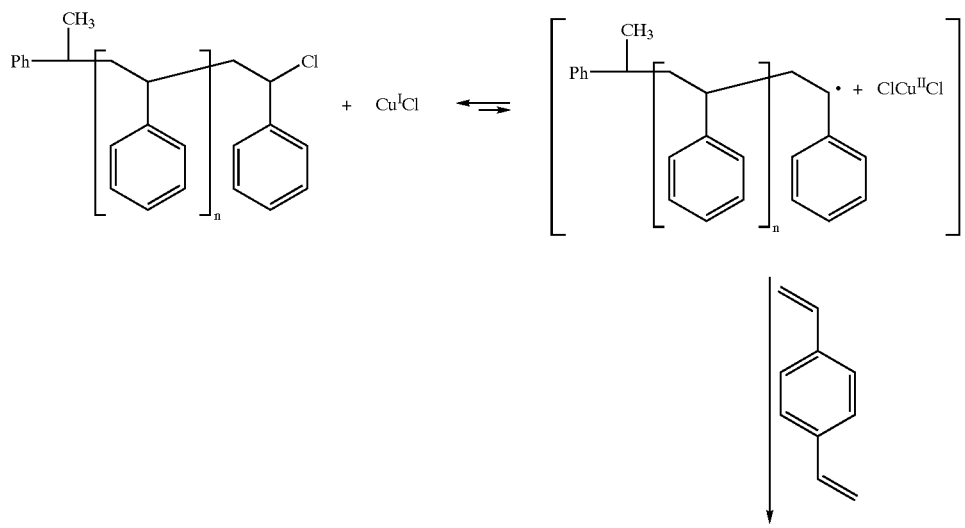

Star microgels

Polystyrene (0.2 g, Mn=4685, Mw/Mn=1.34), end-capped with chlorine atom, was dissolved in benzene (5 ml). To the solution were added 0.05 g divinyl benzene (DVB) in the presence of 1 molar equiv. of CuCl (19 mg) and 3 molar equiv. of bpy (89.9 mg) (both relative to polystyrene). The result mixture was sealed, degassed 3 times and stirred at 130° C. for 24 h. The formed microgel was diluted with THF and filtered before it was precipitated 3 times from methanol as white solid. This was then dried under vacuum before the GPC/MALL System determined the MW.

EXAMPLE 2 a) Preparation of PS Arms End-capped with Br Atom by ATRP Method

FeBr$_2$ (34.0 mg, 0.6 mmol), Styrene (4.86 g, 46.7 mmol), o-xylene (4.0 ml) and N(nBu)$_3$ (0.11 ml, 0.47 mmol) were added to a dry round-bottomed Schlenk flask that was purged with argon. The solution was stirred for 10 minutes at room temperature and then p-toluene-sulfonyl chloride (30.0 mg, 0.16 mmol) was added as a solution in o-xylene (1.0 ml). The flask was sealed and degassed three times to remove oxygen. The flask was then immersed in an oil bath at 80° C. for 8 hours. After polymerization, the solution was diluted with THF. It was then filtered and passed through alumina (Brockmann I, neutral) in a column to remove the complex. The polymer formed was then precipitated from MeOH (3 times) and dried at 60° C. under vacuum for 48 h.

b) Microgel Formation with DVB by ATRP MethodPure Polystyrene with bromine atom capped in the end, received from the above polymerization, was dissolved with o-xylene in a glass tube. To this solution, FeBr$_2$, 1-phenylethyl bromide (1-PEBr) and DVB in appropriate ratio was added. The mixture was then degassed three times before placed into an oil bath at 110° C. After 12 hours polymerization, the microgels was then precipitated from methanol as a white solid.

EXAMPLE 3 a) Preparation of PMMA Arms End-capped with Cl Atom by ATRP Method

Initiation

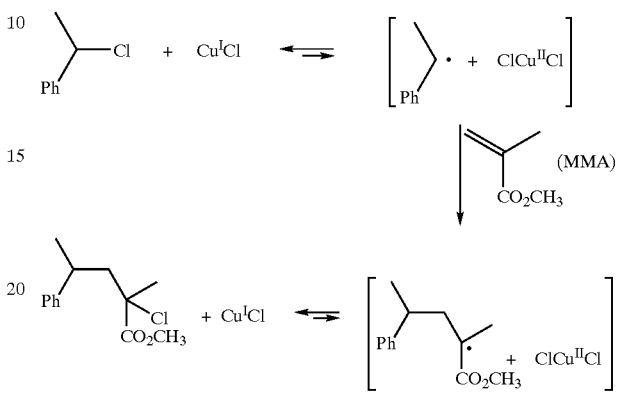

Propagation

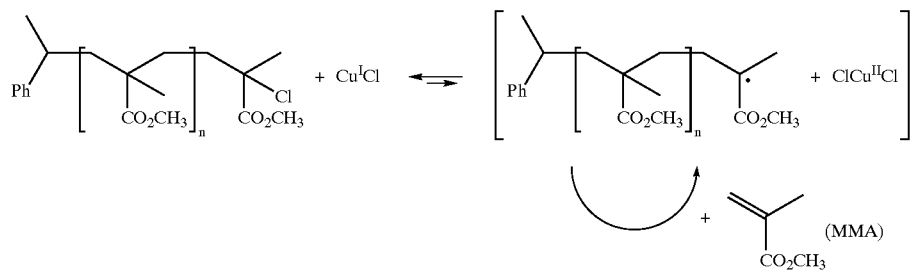

Methyl methacrylate (MMA) (2.63 g, 26.25 mmol), CuCl (0.082 g, 0853 mmol), 2,2'-bipyridine (bpy, 0.389 g, 2.49 mmol) and 1-phenylethyl chloride (1-PECl, 0.116 g, 0.83 mmol) were added into a dry Schlenk flask. The mixture was degassed via 3 freeze-pump-thaw cycles before it was immersed in an oil bath at 130° C. with stirring. After 18 h (overnight) of polymerization, the solution was diluted with THF and heated to 50° C. before filtering. The THF was then evaporated and the residue precipitated from MeOH (3 times) and dried at 60° C. under vacuum for 48 h.

b) Microgel Formation with EGDMA by ATRP Method Crosslinking

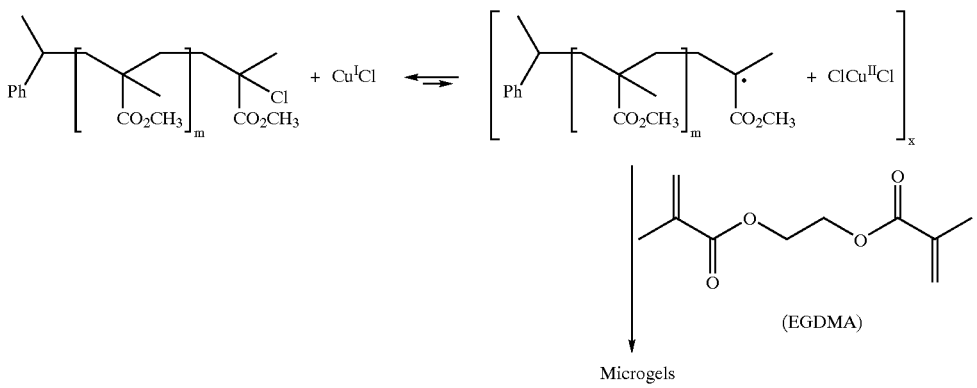

Pure PMMA (0.2 g, 0.063 mmol) end-capped with chlorine atom, was dissolved in o-xylene (5 ml). To the solution were added 0.099 g (0.5 mmol) EGDMA in the presence of 0.018 g (0.063 mmol) of CuCl and 0.06 g (0.190 mmol) of bpy. The result mixture was sealed, degassed 3 times and stirred at 130° C. for 24 h. The formed microgel was diluted with THF and precipitated from methanol as white solid for 3 times.

EXAMPLE 4 a) Preparation of PMMA Arms End-capped with Br Atom by ATRP Method $FeBr_2$ (34.0 mg, 0.16 mmol), MMA (5.0 ml, 46.7 mmol), o-xylene (4.0 ml) and $N(nBU)_3$ (0.11 ml, 0.47 mmol) were added to a dry round-bottomed Schlenk flask that was purged with argon. The solution was stirred for 10 minutes at room temperature and then p-toluene-sulfonyl chloride (30.0 mg, 0.16 mmol) was added as a solution in o-xylene (1.0 ml). The flask was sealed and degassed three times to remove any oxygen. The flask was then immersed in an oil bath at 80° C. for 15 hours. After the reaction, the solution was diluted with THF and filtered. It was then passed through alumina (neutral, activated, Brockmann I) to remove the ions from the complex. The polymer obtained was precipitated from petroleum ether (40° C.–60° C.), and dried under vacuum overnight. The MW of the polymer obtained as measured by GPC is Mn=14707 (PD=1.0767) and the conversion for the reaction is 27.94%.

b) Microgel Formation with EGDMA by ATRP Method

Polymethyl methacrylate (PMMA) (0.3 g, Mn=7488), Ethylene Glycol Dimethacrylate (EGDMA) (0.119 g), $FeBr_2$ (9.8 mg), $N(nBu)_3$ (32.6 μl) and o-xylene (5 ml) were added into a Schlenk flask. The mixture was degassed 3 times. It was then put into an oil bath at 80° C. with stirring. After 14 hours, the solution was diluted with THF and filtered. It was then passed through $Al_2O_3$ and the microgel formed precipitated from petroleum ether (40° C.–60° C.), and dried under vacuum overnight. The molecular weight of the microgels was determined by GPC/MAPLLS system: Mn=6,585,200, PD=1.27.

Further microgels may be prepared by the method described in the Examples 5–18:

EXAMPLE 5 a) Preparation of PMMA Arms End-capped with Br Atom by ATRP Method

PMMA was synthesized in the way as described in Example 4(a).

b) Microgel Formation with DVB by ATRP Method

PMMA, end-capped with bromine atom, was dissolved in o-xylene (10 ml). To the solution was added 0.1 g DVB in the presence of 1 molar equiv. of CuCl and 3 Molar equiv. of bpy (both relative to polystyrene). The result mixture was sealed, degassed 3 times and stirred at 130° C. for 24 h. The formed microgel was precipitated from methanol as white solid. The microgel formed has a strong polar arms and less hydrophilic cores.

EXAMPLE 6 a) Preparation of PS Arms End-capped with Cl Atom by ATRP Method

Polystyrene (PS) was synthesized in the way as described in Example 1(a).

b) Microgel Formation with EGDMA by ATRP Method

PS, end-capped with Cl atom, was dissolved with o-xylene in a glass tube. To this solution, $FeBr_2$, 1-PEBr and EGDMA in the ratio same as before were added. The mixture was then degassed three times before placed into an oil bath at 110° C. After 12 hours polymerization, the microgel was precipitated from methanol as a white solid.

The microgel formed has hydrophobic arms and hydrophilic cores.

EXAMPLE 7 a) Preparation of PMMA Arms End-capped with Br Atom by ATRP Method

PMMA were synthesized in the way as described in Example 4(a).

b) Microgel Formation with AMA/EGDMA by ATRP Method

PMMA (0.3 g, MW=15 000) with bromine atom capped in the end obtained from the above step was dissolved in o-xylene (5 ml) in a Schlenk flask. $FeBr_2$ (9.8 mg), 76 mg of allyl methacrylate (AMA) and EGDMA mixture (1:1 molar ratio) and $N(nBu)_3$ (32.6 μl) were then added. The mixture was stirred for 10 min at room temperature. The flask was then sealed and degassed via 3 freeze-pump-thaw cycles before it was placed in an oil bath at 80° C. After 14 h of polymerization, the solution was diluted with THF, filtered and passed through alumina (Brockmann I, neutral) in a column to remove the metal complex. The microgels formed were precipitated from petroleum ether (40° C.–60° C.) as white solids and dried under vacuum for 24 h.

EXAMPLE 8 a) Preparation of PMMA Arms by Thioester Method

To a round-bottom Schlenk flask was added 25.8 g (0.01) mol of 1-phenylethyl dithiobenzoate in 2 ml toluene, 60 g (0.6 mol) of degassed MMA and 3 mmol of azobisisobutyronitrile (AIBN) in 10 ml toluene. A further 30 ml toluene was added before the mixture was then degassed via 3 freeze-pump-thaw cycles. The sealed flask was then immersed in an oil bath at 80° C. with stirring for 24 h. After the reaction, the solvent was evaporated and the residue was precipitated from MeOH 3 times. The PMMA formed was then dried at 60° C. under vacuum for 48 h. The MW of the polymer obtained as measured by GPC is Mn=20,000 with PD below 1.2.

b) Microgel Formation with EGDMA by Thioester Method

Pure PMMA (Mn=20,000, 2g) with thioester capped from one end obtained from above was dissolved in 20 ml toluene in a round-bottom Schlenk flask. To this solution, 2 g of EGDMA and 0.5 mg of azobisisobutyronitrile (AIBN) were added. The mixture was then degassed via 3 freeze-pump-thaw cycles. The sealed flask was then immersed in an oil bath at 80° C. with stirring for 24 h. After the reaction, the solvent was evaporated and the residue was precipitated from MeOH 3 times. The microgel formed in this way was then dried at 60° C. under vacuum for 48 h.

EXAMPLE 9 a) Preparation of Macromonomers by Chain-transfer Method

To a round-bottom Schlenk flask was added 4 ml of MMA, 0.1 mg of diaquabis(boron difluorodimethylglyoximato) cobaltate in 6 ml of benzene and 20 mg of AIBN. The mixture was then degassed via 3 freeze-pump-thaw cycles, and heated to 60° C. and kept at that temperature for 36 hours. The formed macromonomers were purified by precipitation in pentane and has MW 5000 with PD at 1.5.

b) Microgel Formation from Macromonomers by Radical Polymerization Method

To a round-bottom Schlenk flask was added 2.63 g of pure macromonomers as obtained from above, 2.5 g of EGDMA, 0.5 g of MMA, and 10 mg of AIBN in 5 ml mineral spirits and 15 ml of heptane. After the mixture was degassed via 3 freeze-pump-thaw cycles, it was heated to 60° C. and kept at that temperature for 24 hours. The microgel formed was diluted with THF and precipitated from methanol as white solid 3 times.

EXAMPLE 10 a) Preparation of Macromonomers by Chain-transfer Method

Macromonomers was prepared as described in Example 9a.

b) Conversion of Macromonomers into Cl Atom End-capped Arms by ATRP Method 2.63 g of pure macromonomers obtained from above was dissolved in o-xylene together with 0.082 g of CuCl, 0.389 g of 2,2'-bipyridine and 0.116 g of 1-phenylethyl chloride. The mixture was degassed via 3 freeze-pump-thaw cycles before it was immersed in an oil bath at 130° C. with stirring. After 12 h of reaction, the solution was diluted with THF and heated to 50° C. before filtering. The THF was then evaporated and the residue precipitated from MeOH (3 times) and dried at 60° C. under vacuum for 48 h.

c) Microgel Formation with EGDMA by ATRP Method

Pure PMMA end-capped with chlorine atom was used to produce the microgel using the method as described in Example 3b.

EXAMPLE 11 a) Preparation of Hydroxy Functionalized Macromonomers by Chain-transfer Method

To a round-bottom Schlenk flask was added 4 ml of hydroxyethyl methacrylate (HEA) and MMA in the weight ratio of 8:2, 0.1 mg of diaquabis(boron difluorodimethylglyoximato) cobaltate in 6 ml of methyl ethyl ketone and 20 mg of AIBN. The mixture was then degassed via 3 freeze-pump-thaw cycles, and heated at 60° C. for 36 hours. The hydroxyl formed functionalized macromonomers was purified by precipitation into pentane.

b) Microgel Formation from Hydroxy Functionalized Macromonomers by Radical Polymerization Method To a round-bottom Schlenk flask was added 2.63 g of pure hydroxyl functionalized macromonomers as obtained from above, 2.5 g of EGDMA, 0.5 g of MMA, and 10 mg of AIBN in 5 ml mineral spirits and 15 ml of heptane. The mixture was degassed via 3 freeze-pump-thaw cycles, and heated at 60° C. for 24 hours. The microgel formed was diluted with THF and precipitated from methanol 3 times to form a white solid.

EXAMPLE 12 a) Preparation of Hydroxy Functionalized Macromonomers by Chain-transfer Method

Hydroxy functional macromonomers was prepared as described in Example 11a.

b) Conversion of Hydroxy Functionalized Macromonomers into Cl Atom End-capped Arms by ATRP Method 3.5 g of pure hydroxy functional macromonomers obtained from above was dissolved in o-xylene together with 0.082 g of CuCl, 0.389 g of 2,2'-bipyridine and 0.116 g of 1-phenylethyl chloride. The mixture was degassed via 3 freeze-pump-thaw cycles before it was immersed in an oil bath at 130° C. with stirring. After 12 h of reaction, the solution was diluted with THF and heated to 50° C. before filtering. The THF was then evaporated and the residue precipitated from MeOH (3 times) and dried at 60° C. under vacuum for 48 h.

c) Microgel Formation with EGDMA by ATRP Method

Pure hydroxy functional polymer arms end-capped with chlorine atom (0.063 mmol), was dissolved in o-xylene (5 ml). To the solution were added 0.099 g (0.5 mmol) EGDMA in the presence of 0.018 g (0.063 mmol) of CuCl and 0.06 g (0.190 mmol) of bpy. The resulting mixture was sealed, degassed 3 times and stirred at 130° C. for 24 h. The microgels formed have hydroxy functional groups attached to their arms. The rection solution was diluted with THF and precipitated from methanol as white solid 3 times.

EXAMPLE 13 a) Preparation of Hydroxy Functionalized Macromonomers by Chain-transfer Method

Hydroxy functional macromonomers was prepared as described in Example 11a.

b) Copolymerization of Hydroxy Functionalized Macromonomers with MMA to Form Chlorine Capped Arms by ATRP Method 3.5 g of pure hydroxy functional macromonomers obtained from Example 13a were dissolved in o-xylene (20 ml) together with 2.6 g of MMA, 0.082 g of CuCl, 0.389 g of 2,2'-bipyridine and 0.116 g of 1-phenylethyl chloride. The mixture was degassed via 3 freeze-pump-thaw cycles before it was immersed in an oil bath at 130° C. with stirring. After 12 h of reaction, the solution was diluted with THF and heated to 50° C. before filtering. The THF was then evaporated and the residue precipitated from MeOH (3 times) and dried at 60° C. under vacuum for 48 h. The obtained polymer arms possess hydroxyl functional groups on the half-length of the arms and the other half-length of the arms are unfunctionallized with Cl atom capped in the end.

c) Microgel Formation with EGDMA from Hydroxy Functionalized Copolymer Arms by ATRP Method Pure half-length hydroxy functionalized polymer arms end-capped with chlorine atom (0.063 mmol), was dissolved in o-xylene (5 ml). To the solution were added 0.099 g (0.5 mmol) EGDMA in the presence of 0.018 g (0.063 mmol) of CuCl and 0.06 g (0.190 mmol) of bpy. The resulting mixture was sealed, degassed 3 times and stirred at 130° C. for 24 h. The microgels formed with half-length hydroxy functional group attached on their arms were diluted with THF and precipitated from methanol as white solid 3 times.

EXAMPLE 14 a) Preparation of Macromonomers by Chain-transfer Method

Macromonomers was prepared as described in Example 9a.

b) Conversion of Macromonomers into Cl Atom End-capped Arms by ATRP Method

Chlorine capped PMM arms were converted from macromonomers using the method as described in Example 10b.

c) Microgel Formation with DVB/styrene by ATRP Method

Pure PMMA arms end-capped with chlorine atom (0.063 mmol), was dissolved in o-xylene (5 ml). To the solution were added 0.5 mmol of DVB/styrene mixture (3:7 molar ratio) in the presence of 0.018 g (0.063 mmol) of CuCl and 0.06 g (0.190 mmol) of bpy. The resulting mixture was sealed, degassed 3 times and stirred at 130° C. for 24 h. The microgels formed were diluted with THF and precipitated 3 times from methanol as a white solid.

EXAMPLE 15 a) Preparation of Hydroxy Functionalized Macromonomers by Chain-transfer Method

Hydroxy functional macromonomers was prepared as described in Example 11a.

b) Conversion of Hydroxy Functionalized Macromonomers into Cl Atom End-capped Arms by ATRP Method Chlorine capped hydroxy functional PMM arms were converted from macromonomers using the method as described in Example 12b.

c) Microgel Formation with DVB/styrene by ATRP Method

Pure hydroxy functional PMMA arms end-capped with chlorine atom (0.063 mmol), was dissolved in o-xylene (5 ml). To the solution were added 0.5 mmol of DVB/styrene mixture (3:7 molar ratio) in the presence of 0.018 g (0.063 mmol) of CuCl and 0.06 g (0.190 mmol) of bpy. The resulting mixture was sealed, degassed 3 times and stirred at 130° C. for 24 h. The microgels formed were diluted with THF and precipitated 3 times from methanol as a white solid. These microgels posses the hydrophilic arms and hydrophobic cores.

EXAMPLE 16 a) Preparation of Hydroxy Functionalized Macromonomers by Chain-transfer Method

Hydroxy functional macromonomers was prepared as described in Example 11a.

b) Copolymerization of Hydroxy Functionalized Macromonomers with MMA to form Cl Atom End-capped Arms by ATRP Method Chlorine capped hydroxy functional PMM arms were copolymerized with MMA to form chlorine atom capped arms using the method as described in Example 13b.

c) Microgel Formation with DVB/styrene by ATRP Method

Pure hydroxy functional PMMA arms copolymerized with MMA end-capped with chlorine atom (0.063 mmol), was dissolved in o-xylene (5 ml). To the solution were added 0.5 mmol of DVB/styrene (3:7 ratio) in the presence of 0.018 g (0.063 mmol) of CuCl and 0.06 g (0.190 mmol) of bpy. The resulting mixture was sealed, degassed 3 times and stirred at 130° C. for 24 h. The microgels formed were diluted with THF and precipitated 3 times from methanol as a white solid. The microgels formed in this way posses hydrophilic arms and hydrophobic cores.

EXAMPLE 17 a) Preparation of Hydroxy Functionalized Macromonomers by Chain-transfer Method

Hydroxy functional macromonomers are synthesized in the way described in Example 11a.

b) Hydroxy Functionalized Arms Formation by Addition Reaction

The solution obtained from 11a was diluted with THF and filtered and passed through alumina (Brockmann I, neutral) in a column to remove the metal complex. The macromonomers were then precipitated from methanol as a white solid. The solid was then added with hexadecyltributylphosphonium bromide (0.508 g) and HCl (37%, 12.3 ml) to a round bottom flask. The mixture was stirred and refluxed at 115° C. for 90 min. The organic layer was separated and the aqueous phase extracted with dichloromethane. The solvent was removed and combined organic material dissolved in THF and purified by precipitated from a methanol solution.

c) Microgel Formation with EGDMA by ATRP Method

The hydroxy functional arms (0.3 g) obtained from above with bromine atom capped in the end obtained from the above step was dissolved in o-xylene (5 ml) in a Schlenk flask. $FeBr_2$ (9.8 mg), ethylene glycol dimethacrylate (EGDMA, 0.119 g) and $N(nBu)_3$ (32.6 $\mu$l) were then added. The mixture was stirred for 10 min at room temperature. The flask was then sealed and degassed via 3 freeze-pump-thaw cycles before it was placed in an oil bath at 80° C. After 14 h of polymerization, the solution was diluted with THF, filtered and passed through alumina (Brockmann I, neutral) in a column to remove the metal complex. The microgels formed were then precipitated from petroleum ether (40° C.–60° C.) as a white solids and dried under vacuum for 24 h.

EXAMPLE 18 a) Preparation of Hydroxy Functionalized Macromonomers by Chain-transfer Method

Hydroxy functional macromonomers were synthesized in the way described in Example 11a b) Preparation of Hydroxy Functional Arms End-capped with TEMPO The solution obtained from 11a was diluted with THF, filtered and passed through alumina (Brockmann I, neutral) in a column to remove the metal complex. The macromonomers were then precipitated from methanol as white solid. The solid was added with tert-butyl peroxide (TBP) (4.96 mmol) and tetramethylpiperidin-1-oxyl radical (TEMPO) (0.382 g, 2.45 mmol) in benzene. The mixture was degassed via 3 freeze-pump-thaw cycles and sealed under vacuum. The mixture was heated at 80° C. for 16 h to afford nitroxide capped hydroxy functionalized macromonomers.

c) Microgel Formation with DVB/TBS by TEMPO Method

To TBS (1.14 g, 7.1 mmol) and DVB (0.38 g, 2.9 mmol) in benzene (7.6 ml) was added 1.6 wt % of the hydroxy functional arms obtained from Example 18b with nitroxide capped in the end. The resulting mixture was degassed via

What is claimed is:

1. A process for preparing a microgel composition comprising:

(i) providing a living prepolymer comprising a linear prepolymer and a radical-terminating group adapted to reversibly cleave from the linear prepolymer under activating conditions to provide a reactive linear prepolymer radical wherein the linear prepolymer portion of the living prepolymer comprises a polymeric chain of at least 5 monomer units; and (ii) polymerizing the living prepolymer under activating conditions with a monomer composition comprising a multi-olefinic cross-linking monomer to provide microgel particles comprising a cross-linked polymer core formed from the monomer composition and a multiplicity of linear arms appended to the core said arms being formed from the linear polymer portion of said living prepolymer.

2. A process according to claim 1 wherein the living prepolymer is prepared by reaction of a mono-olefinic monomer and initiator optionally in the presence of a catalyst and has a molecular weight in the range of from 500 to 100,000.

3. A process according to claim 1 said radical-terminating group is selected from the group consisting of lewis acids, mercaptans, disulfides, thiocarbonylthio, thiocarbamates and dithiocarbamates, dithioesters, transition metal carbonyls, stabilized carbon radicals, peroxides and axo compounds.

4. A process according to claim 1 wherein the living prepolymer is prepared by atom transfer radical polymerization or is prepared from iniferters.

5. A process according to claim 1 wherein the living prepolymer is selected from the group consisting of:

(i) compounds of formula $R(A)_n$—X in the presence of a lewis acid catalyst wherein R is an organic residue of a hydrocarbon, alkylsulfonyl or arylsulphonyl and X is halogen;

(ii) thiocarbamates or dithiocarbamates of formula

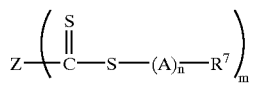

wherein $R^6$ is hydrogen or an initiator fragment residue such as a hydrocarbyl oxide and $R^1$ and $R^2$ are independently selected from hydrocarbyl;

(iii) thioesters of formula

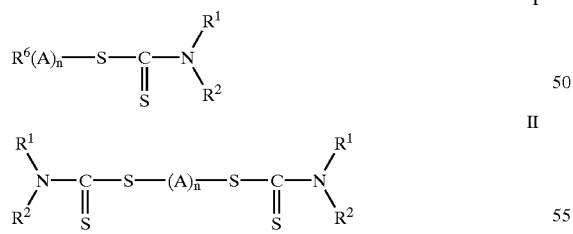

wherein $R^7$ is selected from the group consisting of optionally substituted alkyl, optionally substituted alkenyl, optionally substituted alkynyl, optionally substituted (saturate, unsaturated or aromatic) carbocyclic/heterocyclic ring, optionally substituted alkylthio or a polymer chain and organometallic species;

wherein $R^7$ forms a radical leaving group under the polymerization conditions and is capable of initiating free radical polymerization;

Z is selected from the group consisting of hydrogen, chlorine, optionally substituted alkyl, optional substituted aryl, optionally substituted heterocyclyl, optionally substituted alkylthio, optionally substituted alkoxycarbonyl, optionally substituted aryloxycarbonyl (—COOR"), carboxy (—COOH), optionally substituted acyloxy (—O$_2$CR"), optionally substituted carbamoyl (C—CONR"$_2$), cyano (—CN), dialkyl- or diaryl-phosphonato, and a polymer chain formed by any mechanism, and wherein R" is selected from the group consisting of optionally substituted $C_1$–$C_{18}$ alkyl, $C_2$–$C_{18}$ alkenyl, aryl, heterocyclyl, aralkyl, alkaryl wherein the substituents are independently selected from the group that consists of epoxy, hydroxy, alkoxy, acyl, acyloxy, carboxy (and salts) sulfonic acid (and salts), alkoxy- or aryloxy-carbonyl, isocyanato, cyano, silyl, halo and dialkylamino;

Z' is a multi-valent moiety derived from a member of the group consisting of optionally substituted alkyl, optionally substituted aryl and a polymer chain where the connecting moieties are selected from the group that consists of aliphatic carbon, aromatic carbon, and sulfur;

m and p are integers;

(iv) stabilised carbon radical adducts of formula (V)

wherein $R^3$, $R^4$ and $R^5$ are independently selected from tertiary alkyl and aryl and $R^6$ is an initiator fragment residue selected from tertiary alkyl, aryl and the group —C($R^8R^9R^{10}$) and $R^5R^8R^9$ and $R^{10}$ are independently selected from tertiary alkyl, aryl, nitrate, alkoxy, aryloxy and trimethylsiloxy; and (v) Azo additives of formula VIII

wherein R is hydrocarbyl or alkyl;
(vi) Peroxide additives of formula IX

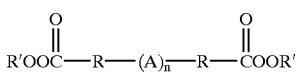

IX wherein R and $R^1$ are hydrocarbyl or alkyl; and
(vii) sulphur trapped adducts of formula XI or XII

          XI

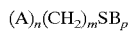          XII wherein A and B are monomers which may be the same or different, n, m and p are integers;
and wherein in the formulas I, II, IIIa, IIIb, V, VIII, IX, XI and XII, the group $(A)_n$ is a prepolymer radical wherein n is an integer of at least 5 and A are independently selected monomeric units.

6. A process according to claim 5 wherein A is independently selected

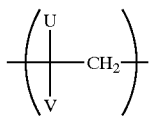

from monomer units of formula and
repeating units from maleic anydride, N-alkylmaleimide, N-arylmalemide, dialkyl fumarate and cyclopolymerizable monomers;
U is selected from the group consisting of hydrogen, halogen, optionally substituted $C_1$–$C_4$ alkyl wherein the substituents are independently selected from the group that consists of hydroxy, alkoxy, aryloxy (OR"), carboxy, acyloxy, aroyloxy ($O_2$CR"), alkoxy-carbonyl and aryloxy-carbonyl ($CO_2$R");
V is selected from the group consisting of hydrogen, R", $CO_2$H, $CO_2$R", COR", CN, $CONH_2$, CONHR", $CONR"_2$, $O_2$CR", OR" and halogen;
wherein R" is selected from group consisting of optionally substituted alkyl, an optionally substituted saturated, unsaturated or aromatic carbocyche or heterocyclic ring; optionally substituted alkylthio; optionally substituted alkoxy, optionally substituted dialkylamino; an organometallic species, and a polymer chain prepared by any polymerization mechanism.

7. A process according to claim 1 wherein the living prepolymer is of Formula XIII

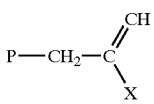          XIII wherein P is a polymer chain comprising at least 5 monomeric units; and
X is —$CONR_2$, —COOR, $OR^1$, —OCOR, —$OCOOR^1$, —$NRCOOR^1$, halo, cyano, or a substituted or unsubstituted phenyl or aryl, wherein R is independently selected from the group of hydrogen, silyl, or a substituted or unsubstituted alkyl, alkyl ether, phenyl, benzyl, or aryl, wherein said groups may be substituted with epoxy, hydroxy, isocyanato, cyano, amino, silyl, acid (—COOH), halo, or acyl; and wherein $R^1$ is the same as R except not H.

8. A process according to claim 5 wherein the living prepolymer provides a radical having a number average molecular weight of from 1000 to 25,000.

9. A process according to claim 1 wherein the multi-olefinic cross-linking monomer is present in an amount of from 5 to 60 mole percent based on the total polymerizable components.

10. A process according to claim 1 wherein the multi-olefinic cross-linking monomer is selected from the group consisting of divinyl benzene, derivatives of divinyl benzene and compounds of Formula XIV:

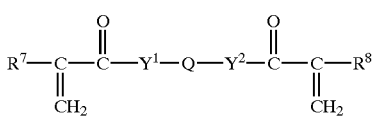      XIV wherein $R^7$ and $R^8$ are independently selected from the group consisting of hydrogen, $C_1$ to $C_6$ alkyl and $C_1$ to $C_6$ hydroxylalkyl; $Y^1$ and $Y^2$ are independently selected from $NR^9$ and O wherein $R^9$ is independently selected from hydrogen and alkyl; and
Q is a linking group optionally substituted with one or more substituents selected from the group consisting of hydroxy, amino, substituted amino, epoxy, silane, acrylate, alkylene acrylate, methacrylate and alkylene methacrylate.

11. A process according to claim 10 wherein the multi-olefinic cross-linking monomer is of Formula XIV and wherein in at least one of the pairs of substituent $R^7$, $R^8$ and $Y^1$, $Y^2$ one of the substituents of the pair is different from the other substituent of said pair.

12. A process according to claim 1 wherein the living prepolymer is present in an amount of at least 5 mole % and the further monomer is present in an amount of up to 80 mole % based on the total numbers of moles of polymerizable composition.

13. A process according to claim 5 wherein the living prepolymer is present in an amount of at least 55 to 95 mole % of the total polymerizable component and the monomer composition further comprises up to 45% mole of the total polymerizable components of the further monomer selected from mono-unsaturated monomers and conjugated diene monomers.

14. A process according to claim 5 wherein the monomer units (A) are derived from one or more monomers selected from the group consisting of alkene, acrylates, methacrylates, styrene or styrenic monomers, acrylonitrile or substituted acrylonitrile, conjugated dienes wherein the monomers may optionally be substituted with one or more functional groups selected from halo, hydroxy, amino, carboxyl, mercapto, substitute amino, silane and epoxy.

15. A process according to claim 5 wherein the oligomer (A)n is a block or statistical polymer and at least one of said monomer units has a polar functional group.

16. A process according to claim 1 wherein the microgel has a number average molecular weight of at least $10^4$.

17. A process according to claim 16 wherein the microgel is soluble in organic solvent.

18. A process according to claim 7 wherein the prepolymer of formula XIII is formed by catalytic chain transfer polymerisation using chain transfer agents containing $Co^{2+}$ or $Co^{3-}$.

19. A process according to claim 1 wherein the living prepolymer is formed and reacted with the multi-olefinic cross-linking monomer by a method of atom transfer radical polymerization.

* * * * *